Figures 1, 1A:
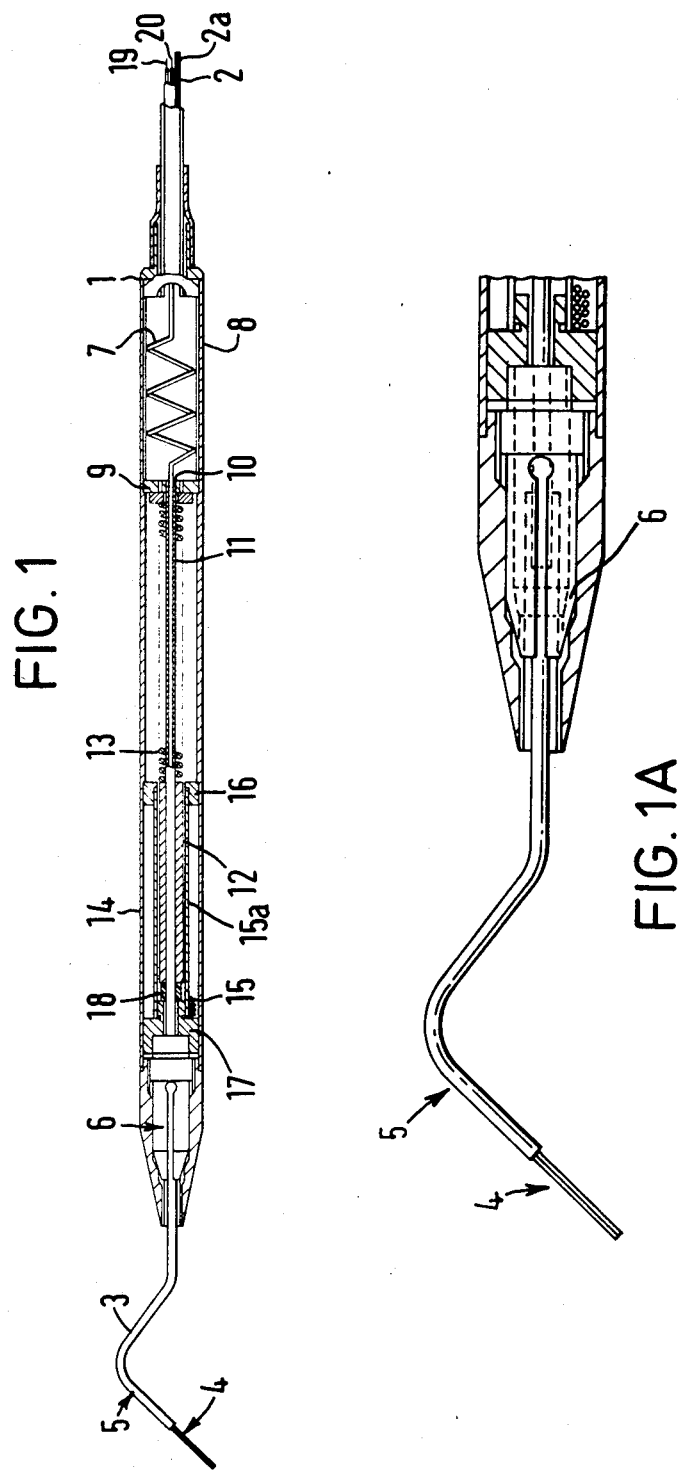

United States Patent [19]

Simon et al.

[11] Patent Number: 4,677,756
[45] Date of Patent: Jul. 7, 1987

[54] MEASURING INSTRUMENTS FOR MEASURING DEPTH OF CAVITIES

[75] Inventors: Lewis A. Simon, Stanmore, England; Michael F. Scarffe, Milton Keynes, United Kingdom

[73] Assignees: VS Remek Limited, Luton; LJS Practice Management Limited, Stanmore, both of England

[21] Appl. No.: 841,754

[22] Filed: Mar. 20, 1986

[30] Foreign Application Priority Data

Mar. 21, 1985 [GB] United Kingdom ............... 8507319

[51] Int. Cl.⁴ .................................................. A61B 5/05
[52] U.S. Cl. ..................................... 33/514; 33/169 B; 33/172 E; 128/776
[58] Field of Search ...................... 33/513, 169 B, 514, 33/172 E; 128/776

[56] References Cited

U.S. PATENT DOCUMENTS

| | | | |
|---|---|---|---|
| 3,058,225 | 10/1962 | Ward | 128/776 X |
| 3,916,529 | 11/1975 | Mousseau | 128/776 X |
| 3,943,914 | 3/1976 | Grenfell et al. | 33/514 X |
| 3,993,044 | 11/1976 | McGuffin | 33/514 |
| 4,526,179 | 7/1985 | Salesky | 128/776 |

FOREIGN PATENT DOCUMENTS

| | | | |
|---|---|---|---|
| 0049905 | 4/1982 | European Pat. Off. | 128/776 |
| 6900409 | 7/1970 | Netherlands . | |
| 2096796 | 10/1982 | United Kingdom . | |

*Primary Examiner*—William D. Martin, Jr.
*Attorney, Agent, or Firm*—Cushman, Darby & Cushman

[57] ABSTRACT

A measuring instrument comprising a pair of probe elements moveable relative to one another to vary the spacing between sensing areas of each probe, means for producing a signal representing the spacing of said sensing areas, means for monitoring the rate of change of said signal, and means for recording and/or displaying a value representative of said signal upon the rate of change of said signal reaching a predetermined value. Preferably there is a probe including a probe element and a sheath, the probe element being slideable within the sheath and protruding therefrom by a variable amount, means for producing a depth signal representing the amount of protrusion of the probe element from the sheath, means for monitoring the rate of change of said depth signal, and means for recording and/or displaying a value representative of said depth signal upon the rate of change of said depth signal reaching a predetermined value.

18 Claims, 7 Drawing Figures

MEASURING INSTRUMENTS FOR MEASURING DEPTH OF CAVITIES

The present invention relates to measuring instruments and has particular applicability to instruments for measuring the depth of cavities, including instruments for measuring the depths of periodontal pockets.

Circumstances arise in which it is necessary to take a series of measurements at different locations and to produce a record of the results associating each result with the location in question. An example of such measurements arises in dental care. In modern dental care, increasing importance is being placed on the treatment of gum disease. An important measure of gum disease is the depth of the cavities or periodontal pockets which are the spaces between the gingival tissues (gums) and the teeth. Probes are available for measuring the depths of these pockets. At present, it is necessary to insert a probe graduated in millimeters to the base of the pocket or cavity and either to take a visual reading of a graduated scale on the instrument or else to provide an electrical signal by operating a switch to actuate a recording device to record a measured value. Such methods are time consuming.

An example of apparatus of this kind is described in U.S. Pat. No. 3,943,914 which describes a dental probe having an electrical sensing mechanism and an operator controlled foot switch connected between the probe and a remote recording device. Whilst use of such an instrument will be faster than the use of the entirely manual instruments it was designed to replace, the need for the user to identify the moment at which a reading should be taken and then to operate the foot switch limits the speed at which the measuring instrument can be used and this becomes signficant when a large number of readings have to be taken. Since it is conventional to take six readings in respect of each tooth, there is room for significant time savings to be made.

European patent specification No. 63778 describes an optical measuring instrument for spectral analysis of living tissues. The instrument is designed to be pressed against tissue to be analysed and to make the necessary measurement automatically when pressed at a predetermined pressure against the tissue. The system employed in the instrument described in specification No. 63778 is not however adapted for use in a distance measuring instrument and cannot readily be adapted for this purpose.

The present invention provides a measuring instrument comprising a pair of probe elements moveable relative to one another to vary the spacing between sensing areas of each probe element, means for producing a signal representing the spacing of said sensing areas, means for monitoring the rate of change of said signal, and means for recording and/or displaying a value representative of said signal upon the rate of change of said signal reaching a predetermined value. Where said predetermined value of the rate of change of the signal at which the measurement is taken is chosen to be substantially zero, such a measuring instrument may be employed by moving the probe elements relative to one another so that the sensing areas of each touch a respective extremity of an item to be measured. As soon as the relative movement of the probe elements ceases a reading is taken and the user may move on to taking the next measurement required.

In particular, the invention provides an instrument for measuring the depth of a cavity comprising a probe including a probe element and a sheath, the probe element being slidable within the sheath and protruding therefrom by a variable amount, means for producing a depth signal representing the amount of protrusion of the probe element from the sheath, means for monitoring the rate of change of the depth signal, and means for recording and/or displaying a value representative of said depth signal upon the rate of change of said depth signal reaching a predetermined value.

Preferably, said recording and/or displaying means is adapted to record and/or display upon the rate of change of said depth signal falling to zero or substantially zero.

Preferably, said recording and/or display means comprises discriminator means for inhibiting, recording or display of depth signal values above and/or below respective predetermined threshold values. Thus, if the sheath is fixed with respect to a body portion or housing of the instrument and the probe element slides therein and is biassed to protrude from the sheath it may be arranged that no values are recorded or displayed when the probe element is stationary at or very close to its maximum protrusion from the sheath. Conversely, in an embodiment in which the probe element is fixed with respect to a body portion or housing of the instrument and the sheath is slidable thereover from a position in which the end of the sheath and the end of the probe element coincide to positions in which the sheath is retracted over the probe element, it may be arranged that no readings are recorded or displayed when the sheath end and the probe element end are substantially together but only when the sheath is retracted over the probe element.

Preferably, the instrument comprises a body portion mounting said sheath and containing a slider connected to said probe element for sliding movement therewith, wherein said means for producing a depth signal derives a signal characteristic of the position of the slider to serve as said depth signal.

Alternatively however, it may be arranged that the instrument comprises a body portion mounting said probe element and containing a slider connected to said sheath for sliding movement therewith, wherein said means for producing a depth signal derives a signal characteristic of the position of said slider to serve as said depth signal.

Periodontal pocket depth measuring instruments have in the past been described which have a probe element extendable with respect to a sheath. In some instruments the sheath is fixed to the body portion of the probe. In others it is the probe element which is fixed and the sheath which is slidable. In specification WO84/03143, a probe is described in which the sheath is fixed to the body portion and a probe element is freely slidable within the sheath but is biassed to protrude from the sheath by a coil spring. A rheostat is provided having a wiper associated with the probe element so that the resistance of the rheostat is a measure of the position of the probe element. It has now been found desirable to provide a method of measuring the position of such a probe element within its sheath which imposes less friction on the movement of the probe element within the sheath than does the use of a rheostat. It has also now been found desirable to provide a more constant resistance to movement of the probe element within the sheath than is provided by a simple compression spring.

Accordingly, the present invention in its preferred embodiments includes an instrument as described above in which said body portion contains an electrical coil winding and a magnetic flux transmitting member, e.g. a core in association with said coil, one of said coil and said member being fixed and the other movable with said slider to vary the inductance of the coil upon movement of the slider, said depth signal producing means deriving a signal representative of said coil inductance to serve as said depth signal.

Preferably the core is movable with the slider and the coil is fixed.

Preferably, the depth signal producing means comprises means for applying a voltage to said coil, switch means for controlling said application of voltage, means for measuring current through said coil, means for operating said switch means to cut off said voltage from said coil when said current exceeds an upper threshold value, means for operating said switch means to apply said voltage to said coil when said current is below a lower threshold value, and frequency measuring means for measuring the frequency of operation of said switch means to provide a signal representing the inductance of the coil.

When the said voltage is applied to the coil, the current through the windings of the coil will rise at a rate dependent on the inductance of the coil. Similarly, when by virtue of the current having exceeded the upper threshold, the voltage is cut off from the coil, the current in the coil will not instantaneously cease but will decay at a rate dependent on the inductance of the coil. Accordingly, the frequency of switching produced by apparatus as described above provides an indication of the coil inductance.

There will be a tendency for the core to locate itself centrally within the coil and if the core is maintained slightly displaced from the central postion, a force will be experienced by the core tending to draw it into the central position. This may be the basis of exercising control over the biassing of the movement of the probe element within the sheath.

Preferably, the coil and core are so arranged with respect to one another that over the whole of a working range of relative positions of said probe element and sheath, application of voltage to said coil produces a force tending to cause displacement of said slider in a constant direction.

Preferably, said force acts to tend to displace said slider such as to cause the probe element to protrude further from the sheath.

Preferably, the instrument further comprises spring means disposed so as to tend to cause the probe element to protrude further from the sheath. The magnetic force acting on the core by virtue of the interaction between the core and the coil will tend to decrease as the core moves further out of the coil. This may be arranged to coincide with an increasing restoring force produced by a suitably arranged compression or tension spring so as to produce an overall substantially constant restoring force tending to push the probe element to protrude from the sheath.

A particular advantage of the use of such a core and coil arrangement is that means may be provided for applying a reset voltage to the coil to provide a force to cause said probe element to protrude from said sheath to a maximum degree to reset said instrument for further use. Generally, it will only be necessary to provide an increased voltage to the coil to force the probe element to protrude from the sheath to the maximum extent. The measurement of the inductance of the coil may be used during the reset procedure as a means of monitoring the relative positions of the probe element and the sheath during the application of said reset signal and the apparatus may be arranged to monitor the relative positions of the probe element and the sheath during the application of the reset signal and to terminate the application of the said signal upon said probe element and the sheath being in a predetermined relative position. This predetermined relative position will normally be with the probe element protruding from the sheath to the maximum extent.

Where the inductance measurement is carried out as described above, it may be arranged that said rest voltage is applied to said coil in conjunction with said upper and lower threshold values so as to apply to the coil a time average voltage higher than that applied during normal depth measuring operations. This will serve to produce a restoring force acting on the probe element considerably higher than that which it experiences during normal use due to the action of core and coil and any spring additionally provided.

Preferably, the means for recording and/or displaying depth signal values comprises data processing means programmed and arranged to record and display sets of readings in a sequence of readings as being associated with particular locations. In particular, the means for recording or displaying depth signal values may comprise data processing means programmed and arranged to record and display sets of readings of depth signal values in a sequence of readings of depth signal values as being associated with particular teeth of the patient.

A further aspect of the diagnosis of gum disease through inspection of periodontal pockets is the determination of the presence or absence of blood in said pockets upon probing. Specification WO84/03143 discloses a method of determining the presence or absence of blood in such sockets which comprises inserting an optical fibre probe into the sockets, which probe has a tapered end, directing light of a particular frequency down the optical fibre into the pocket and measuring the loss of light from the probe to the pocket. Where light is absorbed by blood in the pocket, a more of light is lost to the pocket and less is reflected back along the probe. Such methods may also be employed in a periodontal depth measuring probe in accordance with this invention and accordingly it is preferred that the probe element comprise an optical fibre.

However, it has now been found that superior results may be obtained by an alternative configuration of an optical probe element. Accordingly, the probe element preferably comprises a bundle of optical fibres defining a light transmitting channel and a light receiving channel and all terminating at a free tip end of the probe element.

Preferably, at said probe element tip said light transmitting channel is provided by a central fibre or group of fibres and said light receiving channel by fibres arranged surrounding said central fibre or groups of fibres.

Preferably, the instrument comprises a light source positioned to transmit light through said probe element to be emitted from the free tip of said probe element and means for measuring the intensity of light re-entering said probe tip.

Preferably, the instrument comprises means for transmitting light of at least two distinct wavelengths through said probe element to be emitted from the free tip thereof and for separately measuring the intensity of light at each of said frequencies re-entering the probe tip.

Preferably, said means for transmitting operates to transmit said different wavelengths at different times and preferably a common detector is provided for said different wavelengths. Preferably, the transmitting means comprises light emitting diodes and means for driving said light emitting diodes in short, high intensity pulses.

Light emitting diodes fail thermally when driven at high intensity continuously. We have found that they may be driven at high intensity reliably provided that they are driven only in short pulses. Driving the light emitting diodes in this manner therefore enables the apparatus to operate at much higher light intensity than would be the case using similar light emitting diodes driven continuously and hence increases the sensitivity of the determination performed using the apparatus very considerably.

Preferably, means are provided for taking a ratio of the intensity of light received at a first frequency and that a second frequency. Preferably, the first frequency is chosen as a frequency at which there is relatively little absorbence of the light by blood and the second frequency is chosen as a frequency at which absorbence is comparatively great.

Preferably, the instrument comprises means for automatically making the said optical readings when the rate of change of the signal resulting from the movement of the probe reaches the predetermined value, i.e. preferably when the movement of the probe stops.

Preferably, the apparatus includes means for carrying out a calibration comprising means for recording the signal representing the spacing of the sensing areas of the measuring instrument at a standard spacing, e.g. zero, and preferably also means for recording the ratio of light intensity received at two separate frequencies under calibration conditions.

In accordance with a further aspect of the invention, there is provided a measuring instrument handpiece comprising a first and a second probe element, spacing between sensing areas of the first and second probe elements being variable by relative movement thereof, an electromagnetic coil in close association with a ferromagnetic member, the coil and the member being mounted for relative movement such as to partially withdraw said member from said coil to vary the inductance thereof, one of said coil and said member being connected to said first probe element and the other being connected to the second probe element whereby relative movement of said probe elements produces said relative movement of the member and coil and varies the inductance of the coil.

Figure 2:
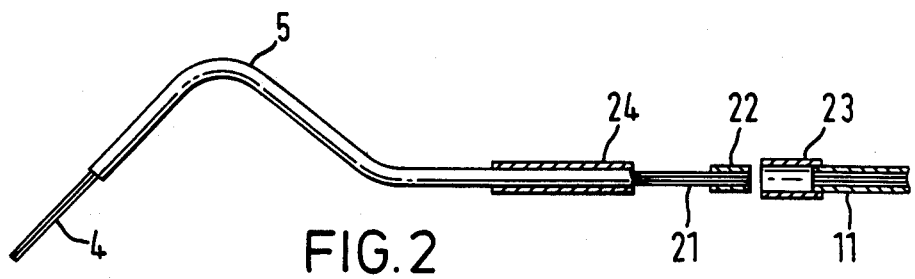
Figure 2A:
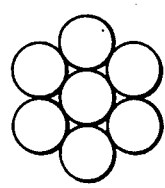
Figure 2B:
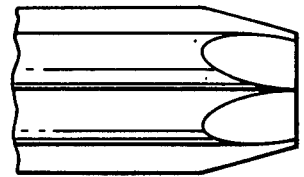
Figure 3:
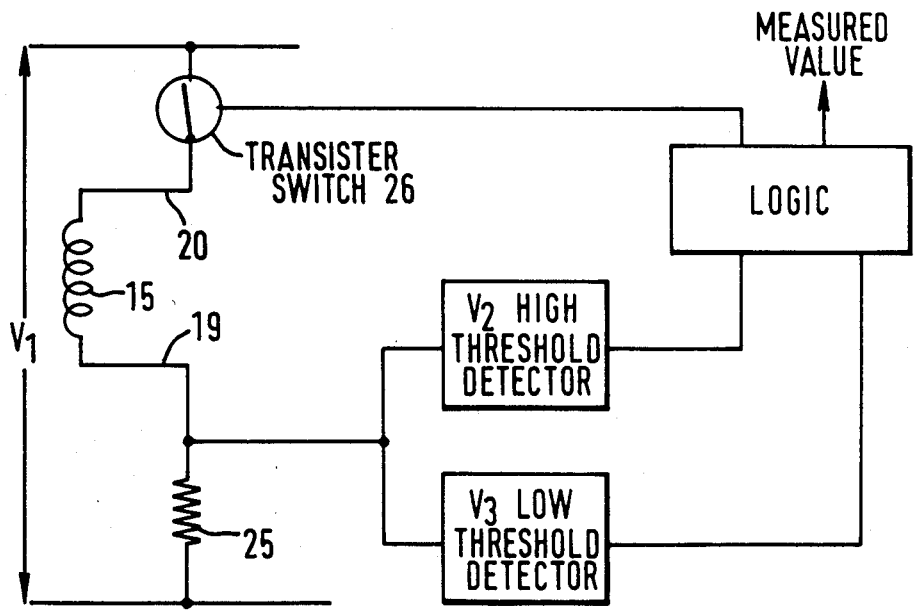
Figure 4:
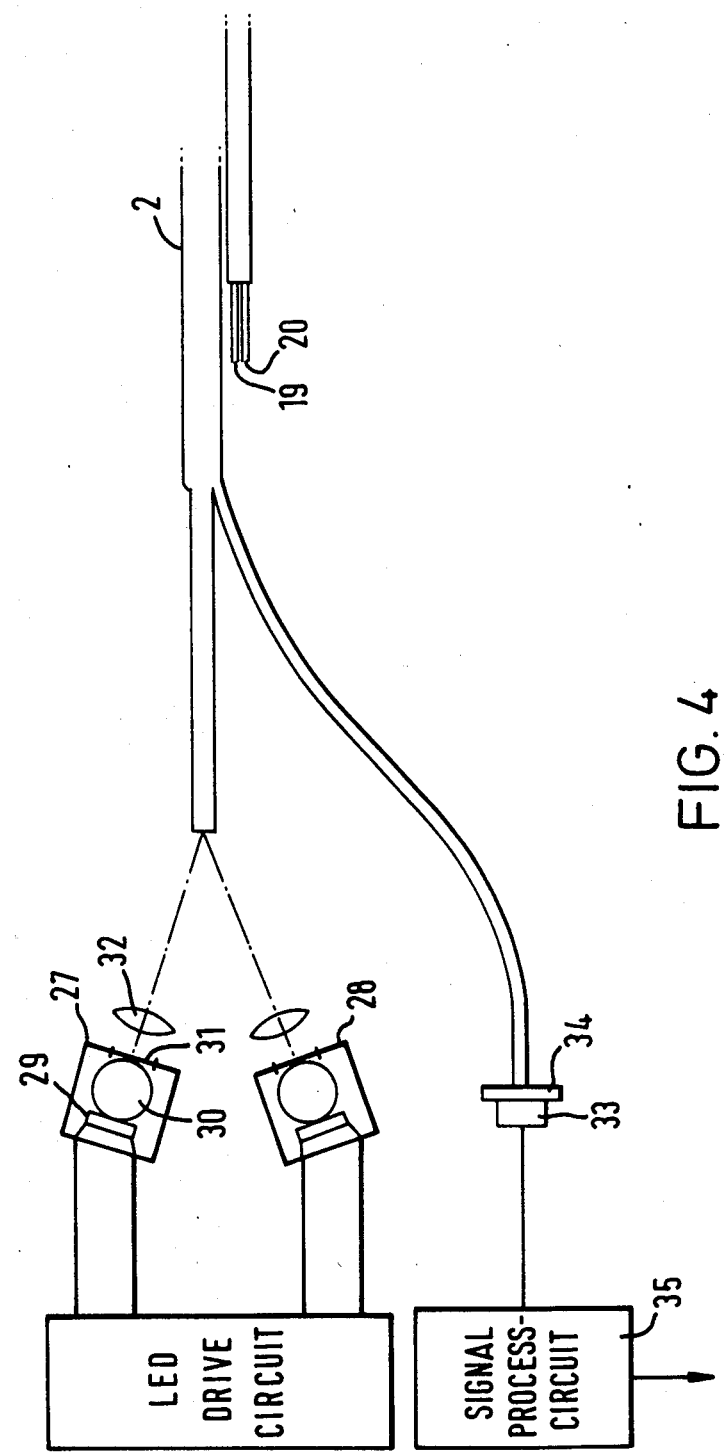

The invention will be further illustrated and explained by the following description of a preferred embodiment with reference to the accompanying drawings in which:

FIG. 1 is an axial cross-sectional view of a measuring instrument hand piece according to the invention, FIG. 1a is an enlarged view of the proximal end of the handpiece of FIG. 1, FIG. 2 is a detail exploded view of the connection between the probe and the body portion of the instrument hand piece of FIG. 1, FIG. 2a is a transverse cross section through the probe element of FIG. 1, FIG. 2b is a side view of the tip of the probe element of FIG. 1, FIG. 3 is a schematic circuit diagram of the depth sensing circuitry of the apparatus and, FIG. 4 is a schematic illustration of the optical measuring system embodied in the apparatus.

The measuring instrument illustrated in FIG. 1 comprises a hand piece 1 connected via a cable 2 to a computer and printer installation (not shown). The hand piece 1 comprises a probe 3 comprising a probe element 4 slidable within a sheath 5. Probe element 4 is made up of a bundle of optical fibres as will be further described hereafter.

The probe 3 is retained within a collet 6 and may be removed therefrom for renewal.

Contained within cable 2 are optical fibres 2a equal in number to those contained within the probe element 4. The optical fibres pass into the rear of the hand piece 1 and form a loose helix 7 in a rear portion of the hand piece. The hand piece has a cylindrical body portion 8 which is divided by a bulk-head 9 into a rear portion containing the loose helix 7 and a forward portion. Bulk-head 9 has a central aperture 10 in which a stainless steel tube 11 is an easy sliding fit. Tube 11 extends forwardly from the bulk-head 9 to the collet 6 and the optical fibres extend through tube 11 and terminate at the forward end thereof as will be described more fully hereafter. The helix 7 accommodates movement of the fibres consequent upon sliding movement of the tube 11.

About a forward part of tube 11 is provided a mild steel ferro-magnetic tubular core 12 which is tightly fitted over the non-magnetic stainless steel tube 11. Between the annular shoulder formed by the rearward end of the core 12 and the tube 11 and the bulk-head 9 is located a compression coil spring 13 tending to bias the tube 11 forwardly. In the region of the core 12, the body portion of the hand member 1 is constituted by a tubular member 14 of mild steel which overlies the core 12 and defines an annular space between the tubular member 14 and the core 12. In the annular space is provided a coil winding 15 wound on the exterior of a stainless steel coil former tube 15a. At the rearward end of the coil winding 15 is an annular end cap of mild steel 16 and at the forward end of the coil is an annular end cap of mild steel 17. The end caps with the tubular member 14 provide a magnetic circuit for flux generated by the coil 15.

Tubular core 12 is a sliding fit within the coil former 15a lubricated by silicone oil. These members form the main bearing for the tube 11. This bearing is of very low friction.

An annular plastic spacer 18 is situated between the end cap 17 and the core 12 preventing the core 12 from achieving a position central with respect to the ends of the coil winding.

Wires connected to the ends of the wire constituting the coil winding extend rearwardly within the hand member 1 and exit from the hand member with the optical fibres 2a at the rearward end therefore in the cable 2 as indicated at 19 and 20.

The structure of the forward end of the handpiece is shown in greater detail in FIG. 1a.

As shown in FIG. 2, the probe 3 is detachable and replaceable. The probe element 4 comprises a bundle of six optical fibres arranged as shown in FIG. 2a with six fibres surrounding a similar central fibre. The fibres are cemented together at the proximal end of the probe where they project from the sheath 5 but within the sheath 5 the fibres run independently. Where the fibres emerge from the distal end of sheath 5 they are once again bonded together over a terminal region 21 and at their extreme distal end they are received within a ferrule 22. At its distal end, sheath 5 bears a collar 24 with which the jaws of the collet 6 engage to retain the probe 3. The tube 11 of the hand piece containing the optical fibres of the hand piece and cable 2 terminates in a guide bush 23 defining a cylindrical aperture within which ferrule 22 is a snug sliding fit. The optical fibres of the hand piece are cemented at the extreme proximal end of the tube 11 in a similar arrangement to that shown in FIG. 2a.

Probe 3 may be attached to the hand piece 1 by gripping the sheath 5 and inserting the distal end thereof through the nose of the collet 6 and pushing the ferrule 22 into the guide bush 23 by means of the collar 24.

When the ferrule 22 has been pushed fully home, collar 24 is withdrawn by a short amount and the collet 6 is then tightened about the collar 24 thus fixing the probe 3 in position.

Due to the arrangement of the optical fibres, it is not necessary to align the fibres rotationally at the join between the hand piece and the probe. The central fibre will automatically be aligned in each case and may be used as an optical transmission channel. The six outer fibres together can constitute an optical receiving channel and the maximum angular misalignment between the probe and the optical fibres of the hand piece will cause only a 20% loss in signal at the junction.

The fibres are lubricated to slide within the sheath 5 by a silicone oil. The lack of bonding of the fibres together within the sheath enables them to slide freely and smoothly.

As shown in FIG. 2b, the end of the probe element 4 is ground to a tapered to a circular end face. The optical fibres may individually be of 0.025 centimeters (0.010 inches) diameter giving rise to a fibre bundle of approximately 0.076 centimeters (0.030 inches) diameter. The end face is chosen to be of diameter 0.051 centimeters (0.020 inches) diameter to comply with an agreed standard for periodontal probe tip diameters.

FIG. 3 illustrates schematically circuitry for connection to the wires 19 and 20 and the coil 15 of the hand piece to provide measurement of the position of the probe element 4.

As shown in FIG. 3, the apparatus comprises as part of a computer/printer unit a source of a driving voltage $V_1$ connected across the coil 15 via a resistor 25 and a transistor switch 26. When transistor switch 26 is closed, current flows through the coil 15 increasing at a rate dependent upon the inductance of the coil 15. The increase in current is monitored by a pair of threshold detectors monitoring the potential drop across resistor 25. When the potential monitored reaches the voltage $V_2$ set on the high threshold detector, this information is passed to the logic circuitry and causes the transistor switch 26 to be opened. The current through the coil 15 then decays at a rate dependent upon its inductance until the potential measured at resistor 25 falls to the voltage $V_3$ set on the low threshold detector. When $V_3$ is reached, the information is passed to the logic circuitry which causes transistor switch 26 to close. Transistor switch 26 therefore closes and opens at a frequency dependent upon the inductance of the coil 15. From this frequency a signal representing of the coil inductance and thus the position of probe element 4 is produced.

The inductance of coil 15 depends upon the position of the tubular sleeve 12 carried by the stainless steel tube 11 and hence upon the position of the probe element 4. The circuitry is arranged to output a value expressed as a measurement of the position of the probe element 4.

The voltage $V_1$ is typically from two to three times the voltage $V_2$. $V_3$ may be only slightly less than $V_2$.

The computer monitors the changes in the frequency and upon a steady value being observed, or a value steady within preset criteria, the computer records and displays a reading of the depth measured. No such readings however are recorded when probe element 4 is at its maximum protruded position, i.e. while the instrument is between measurements. Thus, the logic circuitry may be arranged to store a sequence of values of a signal derived from the frequency of operation of the transistor switch 26 and representative of the inductance of the coil 15 comparing each with previous readings in the series or monitoring the average value of the last few readings so as to detect when the readings become constant to a predetermined degree. When such a degree of constancy is noted, a measured value of the probe position may be output for recording and/or printing.

Reverting to FIG. 1, the tubular core 12, being of ferro-magnetic material, affects the inductance of the coil 15 and the inductance of the coil 15 varies with the position of the tubular core 12, as described above. Accordingly, movement of the tubular core 12 in response to movement of the probe element 4 is detectable by the circuitry of FIG. 5 to provide a measurement of the position of the probe element. A second function of the arrangement shown is that a force is experienced by the tubular core 12 and hence by the tube 11 and the probe element 4 tending to bring the tubular core 12 into a central position within the coil winding 15. Because of the presence of the plastics spacer 18, the tubular core 12 is never able to reach a central position and accordingly the tubular core 12 always experiences force tending to protrude the probe element 4 from the sheath 5. The magnitude of the force depends upon the position of the probe element and upon the voltage applied to the coil 15. The voltage may be selected by suitable choice of voltages $V_1$, $V_2$ and $V_3$. Pushing the probe element 4 further into the sheath 5 in turn pushes the tubular sleeve 12 further out of the region of action of the coil 15 and progressively weakens the force tending to resist such movement experienced by the tubular core 12. The movement however progressively compresses coil spring 13 which provides a steadily increasing resistance. The sum of the forces experienced by the tube 11 and hence by the probe element 4 can be arranged to be very substantially constant. In particular, it can be arranged that a constant force of 25 grams is provided to resist pushing the probe element 4 into the sheath 5.

Alternative means of obtaining such a constant force may however be employed.

A further function of the system illustrated is to provide a reset procedure to push the probe element 4 out to its maximum extent even if there is some degree of resistance. It may be that small particles of debris on the probe element 4 may tend to obstruct free movement of the probe element 4. To force the probe element 4 out to its fullest extent for the commencement of a new measurement or series of measurements, it is sufficient to apply a higher voltage to the coil 15 which then attracts the tubular core 12. Accordingly, by raising the voltages $V_1$, $V_2$ and $V_3$ it is possible to apply substantial force to protrude the probe element 4 and also to continue measurement of the position of the probe element through measurement of the impedance of the coil 15 so as to be able to cease the reset procedure once it is detected that the probe element 4 has reached its maximum displacement position.

The optical functions of the device will be described with reference to FIG. 4.

As shown in FIG. 4, the cable 2 containing the wires 19 and 20 and the optical fibres 2a is connected at its distal end to light transmitting and receiving apparatus driven by suitable circuitry provided by the computer/printer installation. The fibre which is central in the array of fibres at the proximal end of the tube 11 is connected to face a pair of light emitting diodes 27, 28. Each light emitting diode comprises the light emitting area 29 which is situated behind a glass focusing sphere 30 and emits light through a window 31 to pass through a focusing lens 32 to be directed on the end of the fibre. Light emitting diode 27 is chosen to emit light at a frequency of approximately 805 nm whilst diode 28 is selected to emit light at a frequency of about 660 nm. The bundle of fibres which surround the light transmitting fibre at the proximal end of the tube 11 are connected facing a photo detector 33 via a filter 34 which cuts off wavelengths lower than 660 nm. The signals from the photo detector 33 are provided to signal processing circuitry 35.

Conveniently wires 19,20 and fibres 2a can terminate in a single connecting plug which makes with a socket on the computer unit to connect the wires 19 and 20 and to make an optical connection between the light input fibre and diodes 27,28 and between the output fibre bundle and detector 33.

The wavelength of 805 nm is chosen because it is one of those frequencies at which the absorbence of blood is relatively independent of the oxygen saturation level of the blood. The frequency of 660 nm is chosen as a frequency at which the light will strongly be absorbed by blood if any is present.

The LED drive circuit is such as to pulse each light emitting diode in turn with a very short pulse of high current, e.g. about 1 amp. By this means, an output of light tenfold more intense than the LED's are rated for as continuous output may be obtained. The LED's will not be destroyed by this as their mode of failure is thermal and the pulses are sufficiently short that the LED's do not overheat.

The light is emitted from the central fibre of the probe element 4 and light is back scattered into the surrounding fibres of the probe element 4 from the periodontal pocket. If blood is present, then light at the wavelength of 660 nm in particular will be absorbed.

The light is returned through the six fibres forming the return path and is passed through the filter 34 to the photo detector 33 to provide an output signal. Photodetector 63 is chosen to give peak response in the 805 nm region but is still sensitive at 660 nm.

For calibration, the LED's are pulsed in sequence whilst the probe is pressed against a glass plate and the output voltage provided by the photo detector 33 in each case is passed to the signal processing circuitry 35. There, a ratio of the calibration output voltages of the photo detector is taken for the two wavelengths. This may conveniently be termed $Vc_1/Vc_2$.

When the apparatus is used to determine the presence or absence of blood in a periodontal pocket, the LED's are again fired in sequence and the ratio $Vd_1/Vd_2$ being the ratio of the voltages output by photo detector 33 is measured and is divided by the calibration ratios $Vc_1/Vc_2$. In the absence of blood in the periodontal pocket, the ratio will be substantially 1 but in the presence of blood will be likely to be in the region of 7 to 10. The product of the ratios may be compared with a preset threshold value and any reading above the threshold may be output to the printer as an indication that blood is present in the pocket whilst any reading below the threshold may be output as an indication that no blood is present.

The LED drive circuitry may be activated to trigger the LED's in turn upon the probe element 4 ceasing to advance, as monitored by the circuitry shown in FIG. 3.

The computer/printer unit of the instrument may be programmed to permit the following operations. First, the computer may be programmed to expect the calibration procedure in which the probe element 4 is pushed down against a flat surface such as a glass plate to its fullest extent to become flush with the opening of sheath 5. Upon cessation of movement of the probe element 4 being detected by the circuitry of FIG. 3, a value of the inductance corresponding to the maximum retraction of the probe element 4 may be stored as a calibration value in the computer. Simultaneously, the light emitting diode circuitry of FIG. 4 may be triggered to fire each diode in turn once or a plurality of times to produce a calibration value for the $Vc_1/Vc_2$. The probe will then be ready for use.

The computer may also be programmed to expect a series of readings, groups of which are to be allocated to particular teeth. Means may be provided for inputting information into the computer as to the teeth to be tested. This information may be input in the form of indicating teeth which are not present, the remaining teeth all being subjected to the test procedure, or may be inut as a list of teeth to be tested.

To use the probe, the user has then merely to enter the probe element 4 into the periodontal pocket of the first tooth in the sequence advancing the instrument to advance the sheath 5 over the probe element 4 which rests on the bottom of the pocket. Once the sheath 5 of the probe 3 reaches the gum margin, the advance of the probe will be stopped and a reading of the pocket depth will automatically be taken. At the same time, the light emitting diodes will be activated to provide a reading or a series of closely spaced readings of the ratio $Vd_1/Vd_2$ and hence a reading of the presence of absence of blood in the pocket. This procedure will generally be repeated several times, e.g. six times, for each tooth. Preferably, the computer will be programmed to expect three readings to be taken in sequence from each tooth of one jaw of a patient followed by a further three readings from each tooth of the same jaw.

It can be seen that using the apparatus as described above, the taking of readings of periodontal pocket depths and the presence or absence of blood in the pockets upon probing will be greatly speeded and the information is provided to a computer in such a manner that it may be processed and output in any desired form, e.g as a complete chart of the patient's teeth with depth readings and blood indication noted.

Whilst the invention has been described with reference to characteristics of a particular embodiment thereof, it should be appreciated that many modifications and variations thereof are possible within the scope of the invention. For instance, instead of the combination of the magnetic restoring force and a compression spring shown in FIG. 1, one may use a longer coil having a linear force displacement curve in association with a relatively high friction (e.g. about 10 gms) in the probe itself to provide an approximately constant restoring force.

Also, to reduce heating of the coil, the coil may be subjected to voltage to produce the restoring force only during times at which the probe is observed by the circuitry to be moving. At other times, a lower voltage may be employed sufficient only to enable the movement detection to take place.

The detection of blood in a periodontal pocket is made more difficult by the inevitable presence of saliva. Saliva will absorb approximately as strongly as blood at a frequency of 805 nm. At 660 nm blood absorbs considerably more strongly. However as 660 nm is in the visible region, there is a possibility of interference in the analysis by ambient light. In the above described embodiment this is avoided by the firing of diodes 27 and 28 being at a very short time interval, e.g. 1 to 5 milliseconds, typically 2 milliseconds. Any effect of ambient light conducted to the detector 33 will be constant within this period and may therefore be eliminated.

Accordingly, in a further aspect the invention provides an optical measuring instrument comprising first and second flash sources of light (whether or not in the visible region) of different wavelengths, means for subjecting a sample to light from said sources, at closely spaced time intervals, and means for detecting light from said sources after interaction with said sample. Preferably, such an instrument further comprises means for processing signals representative of light intensities received by said detecting means to eliminate the effect of stray light, e.g. by ratioing signals relating to the first and second sources.

Preferably, the closely spaced time intervals are spaced by less than 10 milliseconds, e.g. less than 5 milliseconds. Preferably, said flash durations are less than 2 milliseconds.

Preferably, such an instrument is as described above.

The term "light" is used above to include any form of electromagnetic radiation.

We claim:

1. An instrument for measuring the depth of a cavity comprising:
   a housing member;
   a probe including a probe element and a sheath, said probe element being slidable within said sheath so as to protrude therefrom by a variable amount, one of said probe element and said sheath being mounted to said housing member;
   a slider disposed in said housing member and coupled to one of said probe element and said sheath for sliding movement therewith;
   an electrical coil winding disposed within said housing member;
   a magnetic flux transmitting core disposed within said housing member and operatively coupled to said coil winding, one of said core and said coil winding being fixed relative to said housing member and the other of said core and said coil winding being operatively coupled to said slider so as to be movable therewith to vary the inductance of said coil winding upon movement of said slider;
   means for producing a signal corresponding to the inductance of said coil winding so as to be indicative of the disposition of the slider relative to said housing member thereby constituting a depth signal representative of the amount of protrusion of said probe element from said sheath, said means for producing a signal including:
   (a) means for applying a voltage to said coil winding;
   (b) switch means for controlling said applying means;
   (c) means for measuring current through said coil winding;
   (d) means for operating said switch means so as to cut off said applying means when the measured current exceeds an upper threshold value;
   (e) means for operating said switch means to apply voltage from said applying means when the measured current is below a lower threshold value; and
   (f) frequency measuring means for measuring the frequency of operation of said switch means to produce said signal representative of the inductance of said coil winding;
   means for monitoring the rate of change of said depth signal; and
   means for recording and/or displaying a value corresponding to said depth signal when the rate of change of said depth signal reaches a predetermined value.

2. An instrument as claimed in claim 1, wherein said means for recording and/or displaying records and/or dislays when the rate of change of said depth signal falls to about zero.

3. An instrument as claimed in claim 1 wherein said means for recording and/or display comprises discriminator means for inhibiting recording or display of depth signal values above and/or below respective predetermined threshold values.

4. An instrument as claimed in claim 1, wherein said core is movable with said slider and said coil winding is fixed relative to said housing member.

5. An instrument as claimed in claim 1, wherein said coil winding and said core are disposed relative to one another so that over an entire working range of relative positions of said probe element and said sheath, the application of voltage to said coil winding produces a force tending to displace said slider.

6. An instrument as claimed in claim 5, wherein said force tends to displace said slider so as to urge said probe element outwardly relative to said sheath.

7. An instrument as claimed in claim 5, further comprising spring means disposed within said housing member so as to urge said probe element outwardly relative to said sheath.

8. An instrument as claimed in claim 5, wherein the force is substantially constant over the working range.

9. An instrument as claimed in claim 5, further comprising means for applying a reset signal to said coil winding to urge said probe element to protrude from said sheath a maximum amount so as to reset said instrument for further use.

10. An instrument as claimed in claim 9, further comprising means for monitoring the relative positions of said probe element and said sheath when said reset signal is applied and terminating the application of said reset signal when said probe element and said sheath are in a predetermined relative position.

11. An instrument as claimed in claim 9, wherein said reset signal is applied to said coil winding in conjunction with increasing said upper and lower threshold values so as to apply to said coil winding a time average voltage higher than that applied during normal depth measuring operations.

12. An instrument as claim 1, wherein said means for recording and/or displaying depth signal values comprises data processing means programmed and arranged to record and display sets of readings in a sequence values each being associated with particular teeth of a patient.

13. An instrument as claimed in claim 1 wherein said probe element comprises an optical fibre.

14. An instrument as claimed in claim 13 wherein said probe element comprises a bundle of optical fibres including a light transmitting channel and a light receiving channel.

15. An instrument as claimed in claim 14, wherein at the tip of said probe element said light transmitting channel comprises at least one central fibre and said light receiving channel comprises fibres arranged so as to surround said at least one central fibre.

16. An instrument as claimed in claim 13, further comprising a light source positioned so as to transmit light through said probe element and out of the forward tip of said probe element and means for measuring the intensity of light re-entering said probe tip.

17. An instrument as claimed in claim 16, further comprising means for transmitting light of at least two distinct wavelengths through said probe element and out of from the forward tip thereof and means for separately measuring the intensity of light at each of said frequencies re-entering said probe tip.

18. An instrument as claimed in claim 17 wherein said means for transmitting operates to transmit said different wavelengths at different times and wherein a common detector is provided for said different wavelengths.

* * * * *